United States Patent [19]

Serban et al.

[11] Patent Number: 4,555,263
[45] Date of Patent: Nov. 26, 1985

[54] HERBICIDAL CYCLOHEXANE-1,3-DIONE DERIVATIVES

[75] Inventors: Alexander Serban, Doncaster; Keith G. Watson, Box Hill North; Graham J. Bird, North Melbourne; Graeme J. Farquharson, Reservoir; Timothy L. Houston, Burwood, all of Australia

[73] Assignee: ICI Australia Limited, Victoria, Australia

[21] Appl. No.: 447,137

[22] Filed: Dec. 6, 1982

[30] Foreign Application Priority Data

Dec. 23, 1981 [AU] Australia ............................. PF2072

[51] Int. Cl.$^4$ ..................... A01N 33/24; C07C 131/00
[52] U.S. Cl. ......................................... 71/98; 564/85; 564/256
[58] Field of Search .................. 564/256; 71/98, 106, 71/107, 121; 560/18, 47, 49, 64, 65, 250; 549/79, 561

[56] References Cited

U.S. PATENT DOCUMENTS 3,950,420  4/1976  Sawaki et al. ........................... 71/88
3,989,737  11/1976  Sawaki et al. ........................... 71/98

OTHER PUBLICATIONS

Iwataki, I. et al., Advances in Pesticide Science, Part 2, pp. 235–243, (Pergamon Press (1979)).
Conant, James Bryant et al., *The Chemistry of Organic Compounds*, 4th Ed. (1955), MacMillan Publ. at p. 335.

*Primary Examiner*—N. Trousof
*Assistant Examiner*—L. Hendriksen
*Attorney, Agent, or Firm*—Cushman, Darby & Cushman

[57] ABSTRACT

The invention concerns novel compounds of the formula I

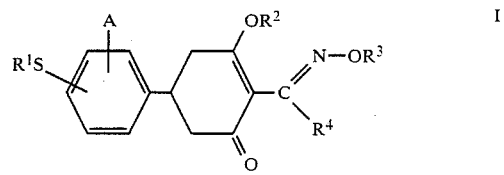

wherein:
$R^1$ is selected from alkyl, alkenyl, alkynyl, cycloalkyl benzyl and substituted benzyl;
A is selected from hydrogen, halogen, nitro, alkyl, alkoxy, alkylthio, alkenylthio, alkynylthio, cycloalkoxy, cycloalkylthio, sulfamoyl, N-($C_1$ to $C_6$ alkyl)sulfamoyl, N,N-di($C_1$ to $C_6$ alkyl)sulfamoyl, benzylthio and substituted benzylthio;
$R^2$ is selected from hydrogen, alkyl, alkenyl, alkynyl, substituted alkyl, acyl, alkylsulfonyl, benzenesulfonyl, substituted benzenesulfonyl, and an inorganic or organic cation;
$R^3$ is selected from alkyl, alkenyl, alkynyl, substituted alkyl, haloalkenyl and haloalkynyl; and
$R^4$ is selected from alkyl, fluoroalkyl, alkenyl, alkynyl and phenyl.

The compounds are herbicides and in further embodiments the invention provides processes for the preparation of compounds of formula I, intermediates useful in the preparation of compounds of formula I, herbicidal compositions containing as active ingredient a compound of formula I, and processes for severely damaging or killing unwanted plants by applying to the plants or to the growth medium of the plants an effective amount of a compound of formula I.

8 Claims, No Drawings

HERBICIDAL CYCLOHEXANE-1,3-DIONE DERIVATIVES

This invention relates to organic compounds having biological activity and in particular to organic compounds having herbicidal properties, to processes for the preparation of such compounds, to intermediates useful in the preparation of such compounds and to herbicidal compositions and processes utilizing such compounds.

The use of certain cyclohexane-1,3-dione derivatives as grass herbicides is known in the art. For example, the "Pesticide Manual" (C. R. Worthing Editor, The British Crop Protection Council, 6th Edition 1979) describes the cyclohexane-1,3-dione derivative known commercially as alloxydim-sodium (methyl 3-[1-(allyloxyimino)butyl]-4-hydroxy-6,6-dimethyl-2-oxocyclohex-3-ene carboxylate) and its use as a grass herbicide. This compound is disclosed in Australian Pat. No. 464 655 and its equivalents such as UK Pat. No. 1 461 170 and U.S. Pat. No. 3 950 420.

More recently, at the 1980 British Crop Protection Conference ("1980 British Crop Protection Conference-Weeds, Proceedings Vol 1, Research Reports", pp 39 to 46, British Crop Protection Council, 1980), a new cyclohexane-1,3-dione grass herbicide code named NP 55 (2-(N-ethoxybutrimidoyl)-5-(2-ethylthiopropyl)-3-hydroxy-2-cyclohexen-1-one) was announced. This compound is disclosed in Australian Patent Application No. AU-Al-35,314/78 and its equivalents.

It has now been found that a new group of cyclohexane-1,3-dione derivatives which have a 5-phenyl substituent which is in turn substituted with an alkylmercapto group exhibit particularly useful herbicidal activity.

Accordingly the invention provides a compound of formula I:

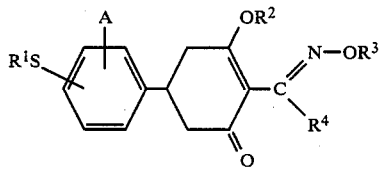

wherein:
$R^1$ is selected from the group consisting of $C_1$ to $C_6$ alkyl, $C_2$ to $C_6$ alkenyl, $C_2$ to $C_6$ alkynyl, $C_3$ to $C_6$ cycloalkyl, benzyl and substituted benzyl wherein the benzene ring is substituted with from one to three substituents selected from the group consisting of halogen, nitro, $C_1$ to $C_6$ alkyl, $C_1$ to $C_6$ alkoxy and $C_1$ to $C_6$ haloalkyl;

A is selected from the group consisting of hydrogen, halogen, nitro, $C_1$ to $C_6$ alkyl, $C_1$ to $C_6$ alkoxy, $C_1$ to $C_6$ alkylthio, $C_2$ to $C_6$ alkenylthio, $C_2$ to $C_6$ alkynylthio, $C_3$ to $C_6$ cycloalkoxy, $C_3$ to $C_6$ cycloalkylthio, sulfamoyl, N-($C_1$ to $C_6$ alkyl)sulfamoyl, N,N-di($C_1$ to $C_6$ alkyl)sulfamoyl, benzylthio and substituted benzylthio wherein the benzene ring is substituted with from one to three substituents selected from the group consisting of halogen, nitro, $C_1$ to $C_6$ alkyl, $C_1$ to $C_6$ alkoxy and $C_1$ to $C_6$ haloalkyl;

$R^2$ is selected from the group consisting of: hydrogen; $C_1$ to $C_6$ alkyl; $C_2$ to $C_6$ alkenyl; $C_2$ to $C_6$ alkynyl; substituted $C_1$ to $C_6$ alkyl wherein the alkyl group is substituted with a substituent selected from the group consisting of $C_1$ to $C_6$ alkoxy, $C_1$ to $C_6$ alkylthio, ($C_1$ to $C_6$ alkoxy)carbonyl, phenyl and substituted phenyl wherein the benzene ring is substituted with from one to three substituents selected from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio; $C_1$ to $C_6$ (alkyl) sulfonyl; benzene sulfonyl; substituted benzenesulfonyl wherein the benzene ring is substituted with from one to three substituents selected from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio; an acyl group; and an inorganic or organic cation;

$R^3$ is selected from the group consisting of: $C_1$ to $C_6$ alkyl; $C_2$ to $C_6$ alkenyl; $C_2$ to $C_6$ haloalkenyl; $C_2$ to $C_6$ alkynyl; $C_2$ to $C_6$ haloalkynyl; substituted $C_1$ to $C_6$ alkyl wherein the alkyl group is substituted with a substituent selected from the group consisting of halogen, $C_1$ to $C_6$ alkoxy, $C_1$ to $C_6$ alkylthio, phenyl and substituted phenyl wherein the benzene ring is substituted with from one to three substituents selected from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio; and $R^4$ is selected from the group consisting of: $C_1$ to $C_6$ alkyl; $C_1$ to $C_6$ fluoroalkyl; $C_2$ to $C_6$ alkenyl; $C_2$ to $C_6$ alkynyl; and phenyl.

When in the compound of formula I $R^2$ is selected from acyl the nature of the acyl group is not narrowly critical. Although not intending to be bound by theory, it is believed that when $R^2$ is acyl the acyl group is removed in the plant by hydrolysis to give the corresponding compound of formula I in which $R^2$ is hydrogen. Suitable acyl groups include: alkanoyl, for example $C_2$ to $C_6$ alkanoyl; aroyl, for example benzoyl and substituted benzoyl wherein the benzene ring is substituted with from one to three substituents selected from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio; and heteroaroyl, for example 2-furoyl, 3-furoyl, 2-thenoyl and 3-thenoyl.

When in the compound of formula I $R^2$ is selected from an inorganic or organic cation the nature of the cation is not narrowly critical. Although not intending to be bound by theory, it is believed that when when $R^2$ is a cation the cation is removed in the plant to give a compound of formula I wherein $R^2$ is hydrogen. Suitable inorganic cations include the alkali and alkaline earth metal ions, heavy metal ions including the transition metal ions, and the ammonium ion. Suitable organic cations include the cation $R^5R^6R^7R^8N^\oplus$ wherein $R^5$, $R^6$, $R^7$ and $R^8$ are independently selected from the group consisting of: hydrogen; $C_1$ to $C_{10}$ alkyl; substituted $C_1$ to $C_{10}$ alkyl wherein the alkyl group is substituted with a substituent chosen from the group consisting of hydroxy, halogen and $C_1$ to $C_6$ alkoxy; phenyl; benzyl; and the groups substituted phenyl and substituted benzyl wherein the benzene ring is substituted with from one to three substituents selected from the group consisting of halogen, nitro, cyano, $C_1$ to $C_6$ alkyl, $C_1$ to $C_6$ haloalkyl, $C_1$ to $C_6$ alkoxy and $C_1$ to $C_6$ alkylthio.

It should be recognized that when $R^2$ is hydrogen the compounds of the invention may exist in any one of three tautomeric forms as shown below:

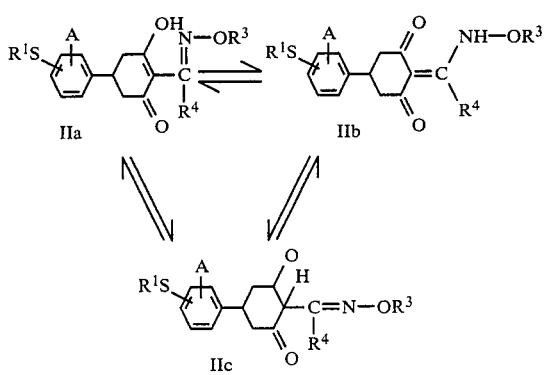

Suitable $R^1$ include $C_1$ to $C_6$ alkyl, $C_2$ to $C_6$ alkenyl, $C_2$ to $C_6$ alkynyl, $C_3$ to $C_6$ cycloalkyl, benzyl and substituted benzyl wherein the benzene ring is substituted with from one to three substituents selected from the group consisting of halogen, nitro, $C_1$ to $C_6$ alkyl, $C_1$ to $C_6$ alkoxy and $C_1$ to $C_6$ haloalkyl.

Suitable A include hydrogen, halogen, nitro, $C_1$ to $C_6$ alkyl, $C_1$ to $C_6$ alkylthio, $C_2$ to $C_6$ alkenylthio, $C_2$ to $C_6$ alkynylthio, $C_3$ to $C_6$ cycloalkylthio, benzylthio and substituted benzylthio wherein the benzene ring is substituted with from one to three substituents selected from the group consisting of halogen, nitro, $C_1$ to $C_6$ alkyl, $C_1$ to $C_6$ alkoxy and $C_1$ to $C_6$ haloalkyl.

Suitable $R^2$ include hydrogen, benzoyl, substituted benzoyl wherein the benzene ring is substituted with from one to three substituents selected from the group consisting of halogen, nitro, $C_1$ to $C_6$ alkyl, $C_1$ to $C_6$ alkoxy and $C_1$ to $C_6$ haloalkyl, and the group M wherein M is an alkali metal ion.

Suitable $R^3$ include $C_1$ to $C_6$ alkyl, $C_2$ to $C_6$ alkenyl, $C_2$ to $C_6$ alkynyl, benzyl and substituted benzyl wherein the benzene ring is substituted with from one to three substituents selected from the group consisting of halogen, nitro, $C_1$ to $C_6$ alkyl, $C_1$ to $C_6$ alkoxy and $C_1$ to $C_6$ haloalkyl.

Suitable $R^4$ include $C_1$ to $C_6$ alkyl.

Preferred $R^1$ include $C_1$ to $C_6$ alkyl, $C_2$ to $C_6$ alkenyl, $C_2$ to $C_6$ alkynyl, benzyl and substituted benzyl wherein the benzene ring is substituted with from one to three substituents selected from the group consisting of halogen, nitro, $C_1$ to $C_6$ L alkyl, $C_1$ to $C_6$ alkoxy and $C_1$ to $C_6$ haloalkyl.

More preferred $R^1$ include $C_1$ to $C_6$ alkyl, $C_2$ to $C_6$ alkenyl, $C_2$ to $C_6$ alkynyl and benzyl.

Even more preferred $R^1$ include $C_1$ to $C_6$ alkyl.

Preferred A include hydrogen, halogen, nitro, $C_1$ to $C_6$ alkyl, $C_1$ to $C_6$ alkoxy, $C_1$ to $C_6$ alkylthio and N,N-di($C_1$ to $C_6$ alkyl)sulfamoyl.

More preferred A include hydrogen, halogen, nitro, $C_1$ to $C_6$ alkyl, $C_1$ to $C_6$ alkylthio and N,N-di($C_1$ to $C_6$ alkyl)sulfamoyl.

Even more preferred A include hydrogen and nitro.

Preferred $R^2$ include: hydrogen; $C_2$ to $C_6$ alkanoyl; benzoyl and substituted benzoyl wherein the benzene ring is substituted with from 1 to 3 substituents selected from the group consisting of halogen, nitro, $C_1$ to $C_6$ alkyl and $C_1$ to $C_6$ alkoxy; and an inorganic or organic cation selected from the alkali metal ions, the alkaline earth metal ions, transition metal ions and the ammonium ion $R^5R^6R^7R^8N^\oplus$ wherein $R^5$, $R^6$, $R^7$ and $R^8$ are independently selected from the group consisting of hydrogen, $C_1$ to $C_{10}$ alkyl and substituted $C_1$ to $C_{10}$ alkyl wherein the alkyl group is substituted with a substituent selected from the group consisting of hydroxy and $C_1$ to $C_6$ alkoxy.

More preferred $R^2$ include hydrogen, acetyl, tertiary-butyryl, benzoyl, halobenzoyl, methylbenzoyl, methoxybenzoyl, nitrobenzoyl, trimethylbenzoyl, dinitrobenzoyl, the cations of the alkali metals sodium and potassium; the cations of the alkaline earth metals magnesium, calcium and barium, the cations of the transition metals manganese, copper, zinc, iron, nickel, cobalt and silver, the ammonium ion, and the tri- and tetra-alkyl ammonium ions wherein alkyl is selected from $C_1$ to $C_6$ alkyl and $C_1$ to $C_6$ hydroxyalkyl.

Even more preferred $R^2$ include hydrogen and the cations of the alkali metal ions.

Preferred $R^3$ include: $C_1$ to $C_6$ alkyl; $C_2$ to $C_6$ alkenyl; $C_2$ to $C_6$ alkynyl; $C_1$ to $C_6$ haloalkyl; $C_2$ to $C_6$ haloalkenyl; $C_1$ to $C_6$ alkyl substituted with $C_1$ to $C_6$ alkoxy; $C_1$ to $C_6$ alkyl substituted with $C_1$ to $C_6$ alkylthio; and benzyl and substituted benzyl wherein the benzene ring is substituted with from one to three substituents selected from the group consisting of halogen, nitro and $C_1$ to $C_6$ alkyl.

More preferred $R^3$ include ethyl, n-propyl, n-butyl, allyl, propargyl, 2-fluoroethyl, 2-chloroallyl, methylthiomethyl, benzyl, halobenzyl, methylbenzyl and nitrobenzyl.

Even more preferred $R^3$ include ethyl and allyl.

Preferred $R^4$ include $C_1$ to $C_6$ alkyl. More preferred $R^4$ include methyl, ethyl and n-propyl. Even more preferred $R^4$ include ethyl and n-propyl.

Particularly preferred compounds of the invention include those compounds of formula I in which the benzene ring is substituted in the 4-position with the group $R^1S$. That is, compounds of formula III:

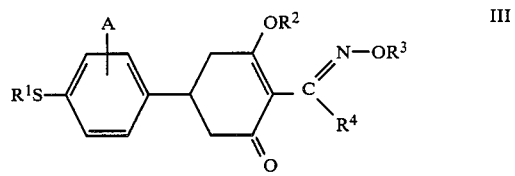

Examples of compounds embraced by the invention include:

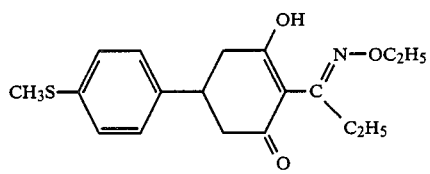

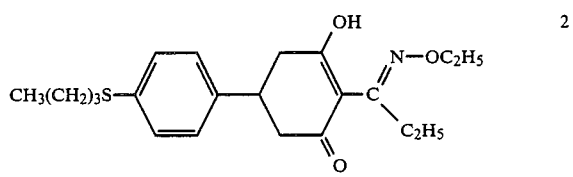

-continued

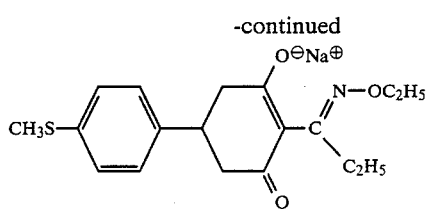
3

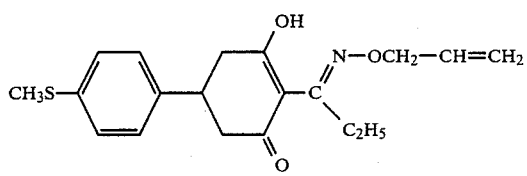
4

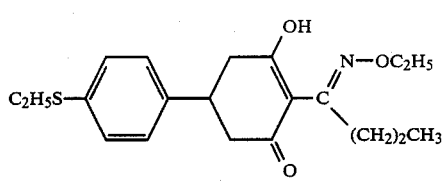
5

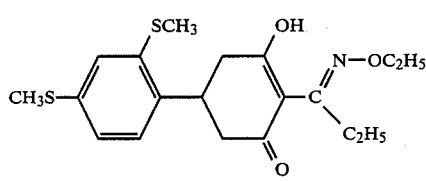
6

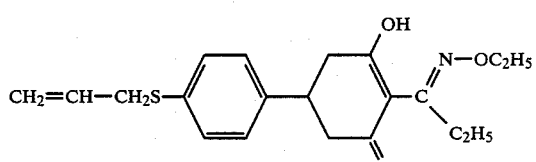
7

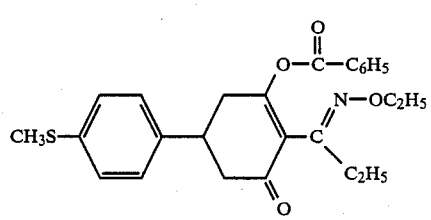
8

Specific examples of the compounds of the invention include those compounds detailed in Table 1 below.

TABLE 1

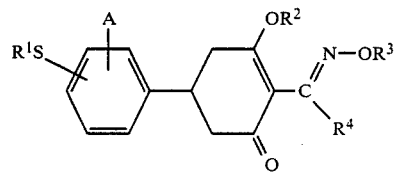

| Compound No | $R^1$ | A | $R^2$ | $R^3$ | $R^4$ |
|---|---|---|---|---|---|
| 1 | 4-CH$_3$ | H | H | C$_2$H$_5$ | C$_2$H$_5$ |
| 2 | 4-CH$_3$ | H | H | C$_2$H$_5$ | C$_2$H$_5$ |
| 3 | 4-CH$_3$ | H | Na | C$_2$H$_5$ | C$_2$H$_5$ |
| 9 | 4-(n-C$_4$H$_9$) | H | H | C$_2$H$_5$ | n-C$_3$H$_7$ |
| 10 | 4-(n-C$_4$H$_9$) | H | H | CH$_2$CH=CH$_2$ | n-C$_3$H$_7$ |
| 11 | 4-(n-C$_4$H$_9$) | 3-NO$_2$ | H | C$_2$H$_5$ | C$_2$H$_5$ |
| 12 | 4-CH$_3$ | 3-SO$_2$N(CH$_3$)$_2$ | H | C$_2$H$_5$ | C$_2$H$_5$ |

TABLE 1-continued

| Compound No | $R^1$ | A | $R^2$ | $R^3$ | $R^4$ |
|---|---|---|---|---|---|
| 13 | 3-CH$_3$ | H | H | C$_2$H$_5$ | C$_2$H$_5$ |

The compounds of the invention may be prepared by a variety of methods and in a further aspect the the invention provides methods for the preparation of compounds of formula I.

Conveniently the preparation of the compounds of the invention can be considered in three or four parts.

Part A involves the formation of a 5-(substituted phenyl)cyclohexane-1,3-dione of formula IX. This reaction may be carried out in a two step process by condensing a benzaldehyde derivative of formula V with acetone to form a ketone of formula VI, which is in turn condensed with a malonic acid ester of formula VII to give a 5-(substituted phenyl)cyclohexane-1,3-dione of formula IX, either with or without the isolation of the intermediate of formula VIII.

Alternatively, this preparation may be carried out in a two step process by condensing a benzaldehyde derivative of formula V with a malonic acid ester of formula VII to give a benzylidenemalonate derivative of formula X which is in turn condensed with an acetoacetic acid ester of formula XI to give a 5-(substituted phenyl)-cyclohexane-1,3-dione of formula IX, either with or without isolation of the intermediate of formula XII.

In a further alternative process this preparation may be carried out by condensing a cinnamate of formula XXI with an acetoacetic acid ester of formula XI to give a 5-(substituted phenyl)cyclohexane-1,3-dione of formula IX, either with or without isolation of the intermediate of formula VIII.

The above reaction sequences are set out in SCHEME A parts (i), (ii) and (iii) respectively below, wherein R represents a C$_1$ to C$_6$ alkyl group.

SCHEME A

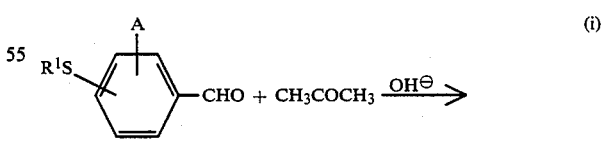 (i)

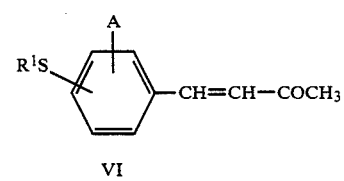

-continued
SCHEME A

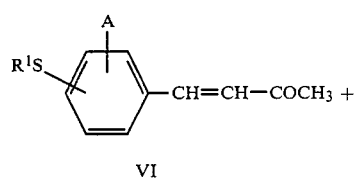

VI $CH_2(CO_2R)_2$ $\xrightarrow{(1) RO^\ominus}_{(2) H^\oplus}$
VII

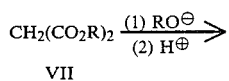

VIII

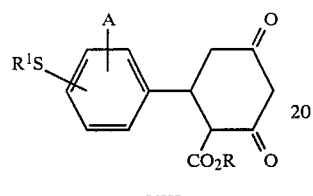

VIII

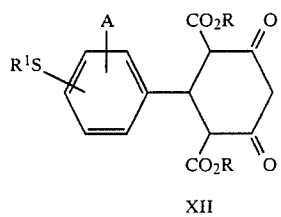

IX (ii)

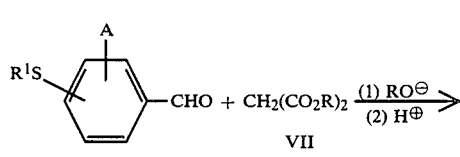—CHO + $CH_2(CO_2R)_2$ $\xrightarrow{(1) RO^\ominus}_{(2) H^\oplus}$
V                          VII

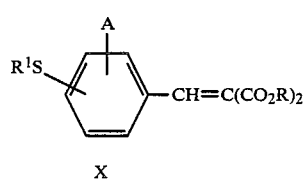

X

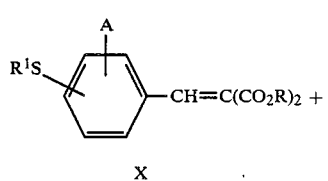—CH=C(CO_2R)_2 +

X $CH_3COCH_2CO_2R$ $\xrightarrow{(1) RO^\ominus}_{(2) H^\oplus}$
XI

-continued
SCHEME A

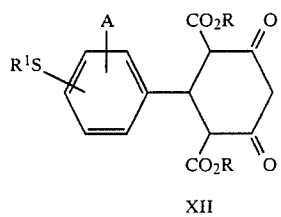

XII

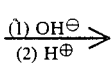

XII $\xrightarrow{(1) OH^\ominus}_{(2) H^\oplus}$

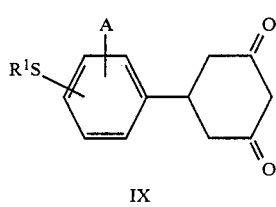

IX (iii)

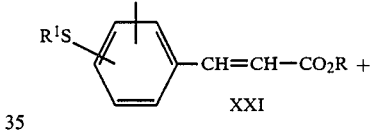—CH=CH—CO_2R +

XXI $CH_3COCH_2CO_2R$ $\xrightarrow{(1) RO^\ominus}_{(2) H^\oplus}$
XI

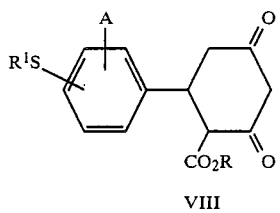

VIII

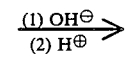

VIII $\xrightarrow{(1) OH^\ominus}_{(2) H^\oplus}$

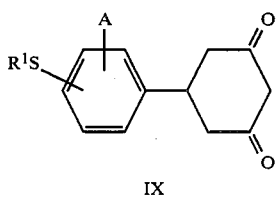

IX

Part B involves the acylation of a compound of formula IX to give a 2-acyl-5-(substituted phenyl)-cyclohexane-1,3-dione of formula XIII. This reaction may be carried out by reacting a 5-(substituted phenyl)-cyclohexane-1,3-dione of formula IX with:

(iv) a mixture of an acid anhydride of formula XIV and either a salt of that acid or an alkoxide salt wherein M is an alkali metal ion and R is $C_1$ to $C_6$ alkyl;

(v) a mixture of an acid anhydride of formula XIV and the corresponding acid;

(vi) an acid halide of formula XV;

(vii) a mixture of an acid halide of formula XV and the corresponding acid; or (viii) an alkali metal or alkaline earth metal hydride followed by reaction with an acid anhydride of formula XIV or an acid halide of formula XV.

Alternatively this reaction may be carried out by:

(ix) reacting a 5-(substituted phenyl)cyclohexane-1,3-dione of formula IX with an acid halide of formula XV in the presence of pyridine to give an intermediate O-acyl derivative of formula XVI; and then:

(x) reacting the intermediate of formula XVI with a Lewis acid catalyst;

(xi) reacting the intermediate of formula XVI with the corresponding acid of the acid halide of formula XV; or (xii) reacting the intermediate of formula XVI with imidazole.

Each of these reactions is outlined in SCHEME B below wherein hal represents halogen.

SCHEME B (iv)

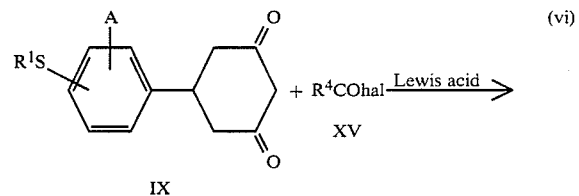

(v)

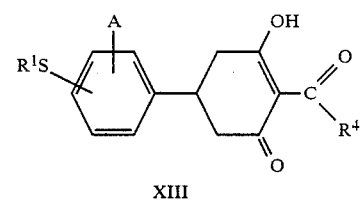

-continued
SCHEME B (vi)

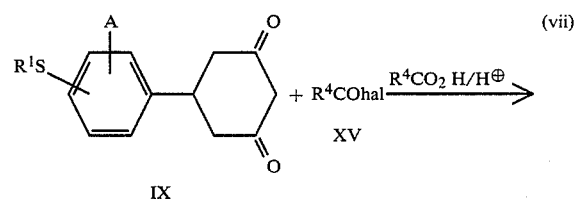

(vii)

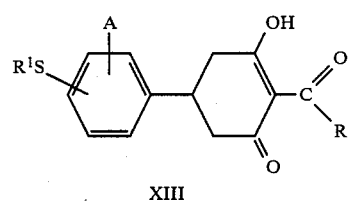

(viii)

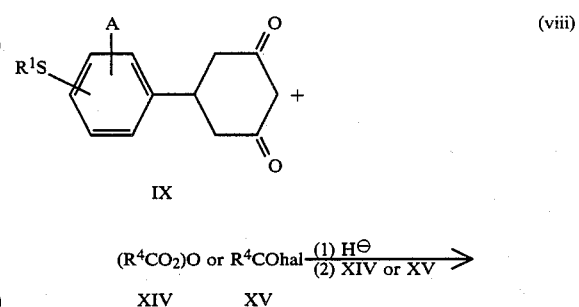

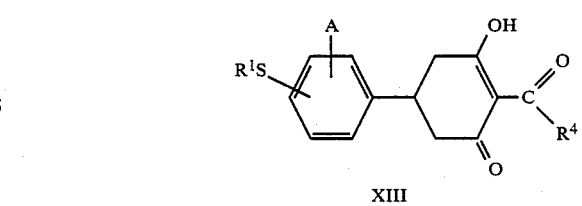

(ix)

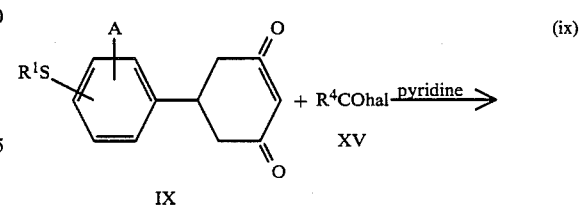

-continued
SCHEME B

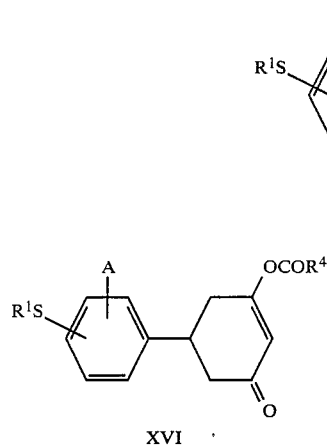

XVI

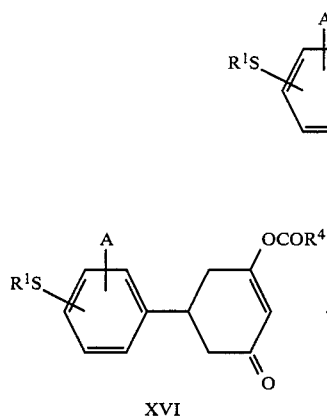

XVI

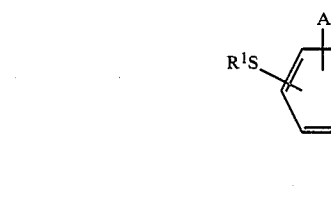

XIII (x)

(xi)

SCHEME C

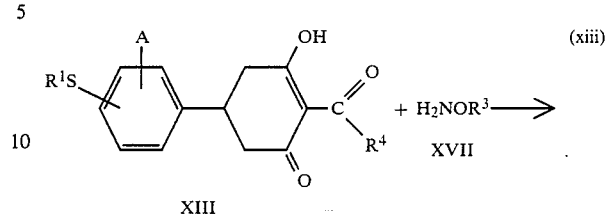

XIII

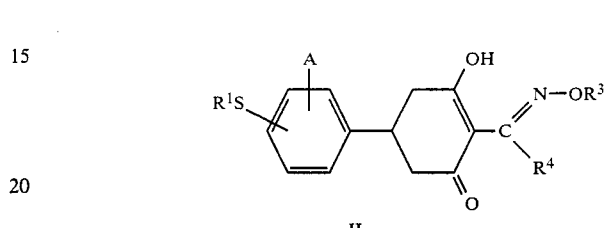

II

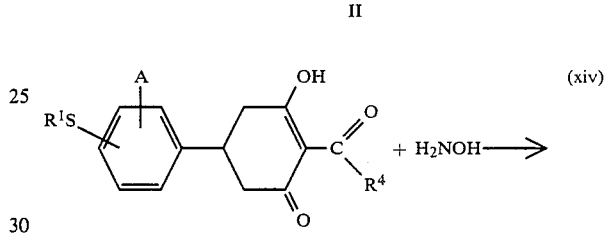

XIII

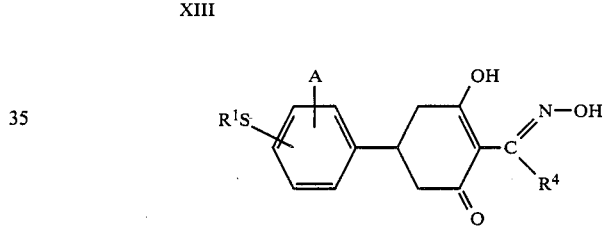

XVIII

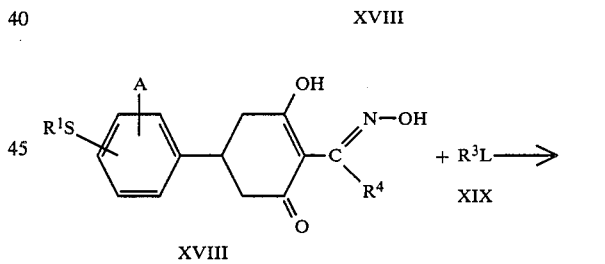

XVIII

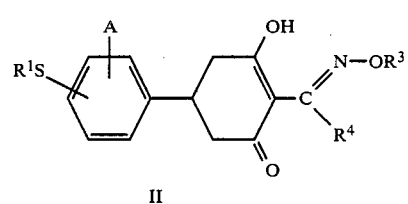

II (xiii)

(xiv)

Part C involves the formation of a compound of the invention of formula I wherein $R^2$ is hydrogen, that is a compound of formula II. This reaction may be carried out either:

(xiii) by reacting a compound of formula XIII with an alkoxyamine derivative of formula XVII to give a compound of formula II; or (xiv) by reacting a compound of formula XIII with hydroxylamine to give an intermediate oxime derivative of formula XVIII and reacting the oxime derivative of formula XVIII with an alkylating agent of formula XIX to give a compound of formula II.

These reaction sequences are set out in SCHEME C below wherein L is a good leaving group such as, for example, chloride, bromide, iodide, sulfate, nitrate, methyl sulfate, ethyl sulfate, tetrafluoroborate, hexafluorophosphate, hexafluoroantimonate, methanesulfonate, fluorosulfonate, fluoromethanesulfonate and trifluoromethanesulfonate.

Compounds of the invention of formula I wherein $R^2$ is an acyl or a sulfonyl group may be prepared from compounds of the invention of formula I wherein $R^2$ is hydrogen, that is, compounds of formula II, by etherification, acylation, or sulfonylation as required. This reaction is outlined in SCHEME D below.

SCHEME D

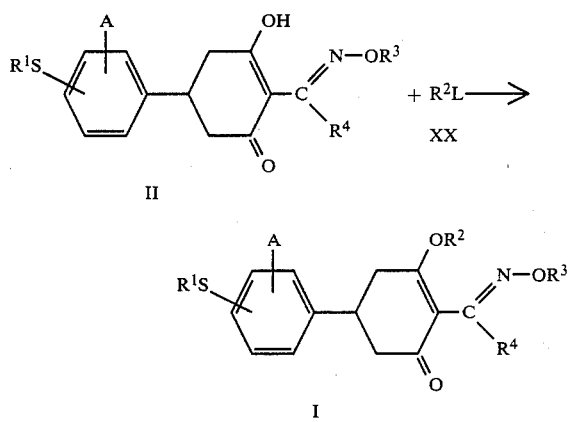

Compounds of the invention of formula I wherein $R^2$ is an inorganic or organic cation may be prepared from the compounds of the invention of formula I wherein $R^2$ is hydrogen, that is, compounds of formula II, by reacting said compounds of formula II with an inorganic or organic salt. For example, the compounds of formula I wherein $R^2$ is an alkali metal ion may be prepared by reacting the appropriate compound of formula II with the appropriate alkali metal hydroxide or alkoxylate. The compounds of formula I wherein $R^2$ is a transition metal ion or an organic cation may similarly be prepared by reacting the appropriate compound of formula II with an appropriate transition metal salt or organic base. Alternatively, the compounds of formula I wherein $R^2$ is a transition metal ion or an organic cation may be prepared by reacting the appropriate compound of formula I wherein $R^2$ is an alkali metal ion with an appropriate transition metal salt or organic salt.

Accordingly, in a further aspect the invention provides a process for the preparation of a compound of formula I, wherein $R^1$, $R^2$, $R^3$ and $R^4$ are as hereinbefore defined, which process comprises:

(a) reacting a benzaldehyde derivative of formula V with acetone to give a ketone derivative of formula VI and reacting the ketone derivative of formula VI with a malonic acid ester of formula VII, wherein R is $C_1$ to $C_6$ alkyl, to give a 5-(substituted phenyl)-cyclohexane-1,3-dione derivative of formula IX; or reacting a benzaldehyde derivative of formula V with a malonic acid ester of formula VII to give a benzylidenemalonate derivative of formula X and reacting the benzylidenemalonate derivative of formula X with an acetoacetic acid ester of formula XI, wherein R is $C_1$ to $C_6$ alkyl, to give a 5-(substituted phenyl)cyclohexane-1,3-dione derivative of formula IX; or reacting a cinnamate of formula XXI, wherein R is $C_1$ to $C_6$ alkyl, with an acetoacetic acid ester of formula XI, wherein R is $C_1$ to $C_6$ alkyl, to give a 5-(substituted phenyl)cyclohexane-1,3-dione derivative of formula IX;

(b) acylating the 5-(substituted phenyl)cyclohexane-1,3-dione derivative of formula IX with an acid anhydride of formula XIV or an acid halide of formula XV togive a 2-acyl-5-(substituted phenyl)cyclohexane-1,3-dione derivative of formula XIII;

(c) reacting the 2-acyl-5-(substituted phenyl)-cyclohexane-1,3-dione derivative of formula XIII with an alkoxyamine derivative of formula XVII to give a compound of the invention of formula II or reacting the 2-acyl-5-(substituted phenyl)cyclohexane-1,3-dione derivative of formula XIII with hydroxylamine and alkylating the oxime intermediate of formula XVIII with an alkylating agent of formula XIX, wherein L is a good leaving group, to give a compound of the invention of formula II; and optionally (d) reacting the compound of the invention of formula II with a compound of formula XX, wherein L is a good leaving group, or reacting the compound of the invention of formula II with an inorganic or organic base or salt, to give a compound of the invention of formula I.

Certain of the intermediate compounds of formulae VI, VIII, IX, X, XII, XXI, XIII, XVI and XVIII are novel compounds and therefore as a further embodiment the invention provides novel compounds of formulae VI, VIII, IX, X, XII, XXI, XIII, XVI and XVIII, wherein the substituents are as hereinbefore defined, and processes for the preparation thereof.

The compounds of formula I are active as herbicides and therefore, in a further aspect the invention provides a process for severely damaging or killing unwanted plants which process comprises applying to the plants, or to the growth medium of the plants, an effective amount of a compound of formula I as hereinbefore defined.

Generally speaking the compounds of formula I are herbicidally effective against a variety of plants. However, certain of the compounds of the invention are selectively active against monocotyledonous plants, dicotyledonous plants being relatively unaffected by rates of application of the compounds of the invention which are severely damaging or lethal to other plant species.

Moreover, certain of the compounds of formula I are selectively active within the group of monocotyledonous plants and may be used at a rate sufficient to kill or severely damage monocotyledonous weeds in a monocotyledonous cereal crop.

Therefore, in yet a further aspect the invention provides a process for selectively controlling the growth of weeds in crops which process comprises applying to the crop, or to the growth medium of the crop, a compound of formula I, as hereinbefore defined, in an amount sufficient to severely damage or kill the weeds but insufficient to damage the crop substantially.

The compounds of formula I may be applied directly to the plant (post-emergence application) or to the soil before the emergence of the plant (pre-emergence application). However, the compounds are, in general, more effective when applied to the plant post-emergence.

The compounds of formula I may be used on their own to inhibit the growth of, severely damage, or kill plants but are preferably used in the form of a composition comprising a compound of the invention in admixture with a carrier comprising a solid or liquid diluent. Therefore, in yet a further aspect the invention provides plant growth inhibiting, plant damaging, or plant killing compositions comprising a compound of formula I as hereinbefore defined and an inert carrier therefor.

The compositions of the present invention may be in the form of solids, liquids or pastes. The compositions include both dilute compositions which are ready for immediate use and concentrated compositions which may require dilution before use. Therefore, the concentration of the active ingredient in the compositions of the present invention will vary depending on the type of formulation and whether the composition is ready for use such as, for example, a dust formulation or an aqueous emulsion or whether the composition is a concentrate such as, for example, an emulsifiable concentrate or a wettable powder, which is suitable for dilution before use. In general the compositions of the present invention comprise from 0.01% to 99% by weight of active ingredient.

The solid compositions may be in the form of powders, dusts, pellets, grains, and granules wherein the active ingredient is mixed with a solid diluent. Powders and dusts may be prepared by mixing or grinding the active ingredient with a solid carrier to give a finely divided composition. Granules, grains and pellets may be prepared by bonding the active ingredient to a solid carrier, for example, by coating or impregnating the preformed granular solid carrier with the active ingredient or by agglomeration techniques.

Examples of solid carriers include: mineral earths and clays such as, for example, kaolin, bentonite, kieselguhr, Fuller's earth, Attaclay, diatomaceous earth, bole, loess, talc, chalk, dolomite, limestone, lime, calcium carbonate, powdered magnesia, magnesium oxide, magnesium sulfate, gypsum, calcium sulfate, pyrophyllite, silicic acid, silicates and silica gels; fertilizers such as, for example, ammonium sulfate, ammonium phosphate, ammonium nitrate and urea; natural products of vegetable origin such as, for example, grain meals and flours, bark meals, wood meals, nutshell meals and cellulosic powders; and synthetic polymeric materials such as, for example, ground or powdered plastics and resins.

Alternatively, the solid compositions may be in the form of dispersible or wettable dusts, powders, granules or grains wherein the active ingredient and the solid carrier are combined with one or more surface active agents which act as wetting, emulsifying and/or dispersing agents to facilitate the dispersion of the active ingredient in liquid.

Examples of surface active agents include those of the cationic, anionic and non-ionic type. Cationic surface active agents include quaternary ammonium compounds, for example, the long chain alkylammonium salts such as cetyltrimethylammonium bromide. Anionic surface active agents include: soaps or the alkali metal, alkaline earth metal and ammonium salts of fatty acids; the alkali metal, alkaline earth metal and ammonium salts of ligninsulfonic acid; the alkali metal, alkaline earth metal and ammonium salts of arylsulfonic acids including the salts of naphthalenesulfonic acids such as butylnaphthalenesulfonic acid, the di- and triisopropylnaphthalenesulfonic acids, the salts of the condensation products of sulfonated naphthalene and naphthalene derivatives with formaldehyde, the salts of the condensation products of sulfonated naphthalene and naphthalene derivatives with phenol and formaldehyde, and the salts of alkylarylbenzenesulfonic acids such as dodecylbenzenesulfonic acid; the alkali metal, alkaline earth metal and ammonium salts of the long chain mono esters of sulfuric acid or alkylsulfates such as laurylsulfate and the mono esters of sulfuric acid with fatty alcohol glycol ethers. Nonionic surface active agents include: the condensation products of ethylene oxide with fatty acohols such as oleyl alcohol and cetyl alcohol; the condensation products of ethylene oxide with phenols and alkylphenols such as isooctylphenol, octylphenol and nonylphenol; the condensation products of ethylene oxide with castor oil; the partial esters derived from long chain fatty acids and hexitol anhydrides, for example sorbitan monolaurate, and their condensation products with ethylene oxide; ethylene oxide/propylene oxide block copolymers; lauryl alcohol polyglycol ether acetal; and the lecithins.

The liquid compositions may comprise a solution or dispersion of the active ingredient in a liquid carrier optionally containing one or more surface active agents which act as wetting, emulsifying and/or dispersing agents. Examples of liquid carriers include: water; mineral oil fractions such as, for example, kerosene, solvent naphtha, petroleum, coal tar oils and aromatic petroleum fractions; aliphatic, cycloaliphatic and aromatic hydrocarbons such as, for example, paraffin, cyclohexane, toluene, the xylenes, tetrahydronaphthalene and alkylated naphthalenes; alcohols such as, for example, methanol, ethanol, propanol, isopropanol, butanol, cyclohexanol and propylene glycol; ketones such as, for example, cyclohexanone and isophorone; and strongly polar organic solvents such as, for example, dimethylformamide, dimethylsulfoxide, N-methylpyrrolidone and sulfolane.

A preferred liquid composition comprises an aqueous suspension, dispersion or emulsion of the active ingredient which is suitable for application by spraying, atomizing or watering. Such aqueous compositions are generally prepared by mixing concentrated compositions with water. Suitable concentrated compositions include emulsion concentrates, pastes, oil dispersions, aqueous suspensions and wettable powders. The concentrates are usually required to withstand storage for prolonged periods and after such storage to be capable of dilution with water to form aqueous preparations which remain homogeneous for a sufficient time to enable them to be applied by conventional spray equipment. The concentrates conveniently contain from 20 to 99%, preferably 20 to 60%, by weight of active ingredient.

Emulsion or emulsifiable concentrates are conveniently prepared by dissolving the active ingredient in an organic solvent containing one or more surface active agents. Pastes may be prepared by blending the finely divided active ingredient with a finely divided solid carrier, one or more surface active agents and optionally an oil. Oil dispersions may be prepared by grinding together the active ingredient, a hydrocarbon oil, and one or more surface active agents. Aqueous suspension concentrates may conveniently be prepared by ball milling a mixture of the active ingredient, water, at least one surface active agent and preferably at least one suspending agent. Suitable suspending agents include: hydrophilic colloids such as, for example, poly(N-vinylpyrrolidone), sodium carboxymethylcellulose and the vegetable gums gum acacia and gum tragacanth; hydrated colloidal mineral silicates such as, for example, montmorillonite, beidellite, nontronite, hectorite, saponite, sauconite and bentonite; other cellulose derivatives; and poly(vinyl alcohol). Wettable powder concentrates may conveniently be prepared by blending together the active ingredient, one or more surface active agents, one or more solid carriers and optionally one or more suspending agents and grinding the mixture to give a powder having the required particle size.

The aqueous suspensions, dispersions or emulsions may be prepared from the concentrated compositions by mixing the concentrated compositions with water optionally containing surface active agents and/or oils.

It should be noted that the compounds of the invention of formula I wherein $R^2$ is hydrogen are acidic. Therefore, the compounds of formula I may be formulated and applied as the salts of organic or inorganic bases. In formulating and employing the compounds of formula I in the form of their salts either the salts per se, that is the compounds of formula I wherein $R^2$ is an inorganic or an organic cation, may be used in the formulation or the compounds of formula I wherein $R^2$ is hydrogen may be used in the formulation and the salts generated in situ by the use of the appropriate organic or inorganic base.

The mode of application of the compositions of the invention will depend to a large extent on the type of composition used and the facilities available for its application. Solid compositions may be applied by dusting or any other suitable means for broadcasting or spreading the solid. Liquid compositions may be applied by spraying, atomizing, watering, introduction into the irrigation water, or any other suitable means for broadcasting or spreading the liquid.

The rate of application of the compounds of the invention will depend on a number of factors including, for example, the compound chosen for use, the identity of the plants whose growth is to be inhibited the formulations selected for use and whether the compound is to be applied for foliage or root uptake. As a general guide, however, an application rate of from 0.005 to 20 kilograms per hectare is suitable while from 0.01 to 5.0 kilograms per hectare may be preferred.

The compositions of the invention may comprise, in addition to one or more compounds of the invention, one or more compounds not of the invention but which possess biological activity. For example, as hereinbefore indicated the compounds of the invention are in general substantially more effective against monocotyledonous plants or grass species than against dicotyledonous plants or broad-leaved species. As a result, in certain applications the herbicidal use of the compounds of the invention alone may not be sufficient to protect a crop. Accordingly in yet a still further embodiment the invention provides a herbicidal composition comprising a mixture of at least one herbicidal compound of formula I as hereinbefore defined with at least one other herbicide.

The other herbicide may be any herbicide not having the formula I. It will generally be a herbicide having a complementary action. For example, one preferred class is of mixtures comprising a herbicide active against broad-leaved weeds. A second preferred class is of mixtures comprising a contact herbicide.

Examples of useful complementary herbicides include:

A. benzo-2,1,3-thiadiazin-4-one-2,2-dioxides such as 3-isopropylbenzo-2,1,3-thiadiazin-4-one-2,2-dioxide (common name bentazon);
B. hormone herbicides and in particular the phenoxyalkanoic acids such as 4-chloro-2-methylphenoxy acetic acid (common name MCPA), 2-(2,4-dichlorophenoxy)propionic acid (common name dichlorprop), 2,4,5-trichlorophenoxyacetic acid (common name 2,4,5-T), 4-(4-chloro-2-methylphenoxy)butyric acid (common name MCPB), 2,4-dichlorophenoxyacetic acid (common name 2,4-D), 4-(2,4-dichlorophenoxy)butyric acid (common name 2,4-DB), 2-(4-chloro-2-methylphenoxy)propionic acid (common name mecoprop), and their derivatives (eg salts, esters, amides and the like);
C. 3-[4-(4-halophenoxy)phenyl]-1,1-dialkylureas such as 3-[4-(4-chlorophenoxy)phenyl]-1,1-dimethylurea (common name chloroxuron);
D. dinitrophenols and their derivatives (eg acetates) such as 2-methyl-4,6-dinitrophenol (common name DNOC), 2-tertiarybutyl-4,6-dinitrophenol (common name dinoterb), 2-secondarybutyl-4,6-dinitrophenol (common name dinoseb) and its ester dinoseb acetate;
E. dinitroaniline herbicides such as N',N'-diethyl-2,6-dinitro-4-trifluoromethyl-m-phenylenediamine (common name dinitramine), 2,6-dinitro-N,N-dipropyl-4-trifluoromethylaniline (common name trifluralin) and 4-methylsulfonyl-2,6-dinitro-N,N-dipropylaniline (common name nitralin);
F. phenylurea herbicides such as N'-(3,4-dichlorophenyl)-N,N-dimethylurea (common name diuron) and N,N-dimethyl-N'-[3-(trifluoromethyl)phenyl]urea (common name fluometuron);
G. phenylcarbamoyloxyphenylcarbamates such as 3-[(methoxycarbonyl)amino]phenyl (3-methylphenyl)-carbamate (common name phenmedipham) and 3-[(ethoxycarbonyl)amino]phenyl phenylcarbamate (common name desmedipham);
H. 2-phenylpyridazin-3-ones such as 5-amino-4-chloro-2-phenylpyridazin-3-one (common name pyrazon);
I. uracil herbicides such as 3-cyclohexyl-5,6-trimethyleneuracil (common name lenacil), 5-bromo-3-sec-butyl-6-methyluracil (common name bromacil) and 3-tert-butyl-5-chloro-6-methyluracil (common name terbacil);
J. triazine herbicides such as 2-chloro-4-ethylamino-6-(iso-propylamino)-1,3,5-triazine (common name atrazine), 2-chloro-4,6-di(ethylamino)-1,3,5-triazine (common name simazine) and 2-azido-4-(iso-propylamino)-6-methylthio-1,3,5-triazine (common name aziproptryne);
K. 1-alkoxy-2-alkyl-3-phenylurea herbicides such as 3-(3,4-dichlorophenyl)-1-methoxy-1-methylurea (common name linuron), 3-(4-chlorophenyl)-1-methoxy-1-methylurea (common name monolinuron) and 3-(4-bromo-4-chlorophenyl)-1-methoxy-1-methylurea (common name chlorobromuron);
L. thiolcarbamate herbicides such as S-propyl dipropylthiocarbamate (common name verolate);
M. 1,2,4-triazin-5-one herbicides such as 4-amino-4,5-dihydro-3-methyl-6-phenyl-1,2,4-triazine-5-one (common name metamitron) and 4-amino-6-tert-butyl-4,5-dihydro-3-methylthio-1,3,4-triazin-5-one (common name metribuzin);
N. benzoic acid herbicides such as 2,3,6-trichlorobenzoic acid (common name 2,3,6-TBA), 3,6-dichloro-2-methoxybenzoic acid (common name dicamba) and 3-amino-2,5-dichlorobenzoic acid (common name chloramben).
O. anilide herbicides such as N-butoxymethyl-α-chloro-2',6'-diethylacetanilide (common name butachlor), the corresponding N-methoxy compound (common name alachlor), the corresponding N-iso-propyl compound (common name propachlor) and 3',4'-dichloropropionanilide (common name propanil);
P. dihalobenzonitrile herbicides such as 2,6-dichlorobenzonitrile (common name dichlobenil), 3,5-dibromo-4-hydroxybenzonitrile (common name bromoxynil) and 3,5-diiodo-4-hydroxybenzonitrile (common name ioxynil);
Q. haloalkanoic herbicides such as 2,2-dichloropropionic acid (common name dalapon), trichloroacetic acid (common name TCA) and salts thereof;
R. diphenylether herbicides such as 4-nitrophenyl 2-nitro-4-trifluoromethylphenyl ether (common name fluorodifen), methyl 5-(2,4-dichlorophenoxy)-2- nitrobenzoate (common name bifenox), 2-nitro-5-(2-chloro-4-trifluoromethylphenoxy)benzoic acid and 2-chloro-4-trifluoromethylphenyl 3-ethoxy-4-nitrophenyl ether;

S. N-(heteroarylaminocarbonyl)benzenesulfonamides such as 2-chloro-N-[(4-methoxy-6-methyl-1,3,5-triazin-2-yl)aminocarbonyl]benzenesulfonamide (commonly known as DPX 4189); and T. miscellaneous herbicides including N,N-dimethyldiphenylacetamide (common name diphenamid), N-(1-naphthyl)phthalamic acid (common name naptalam) and 3-amino-1,2,4-triazole.

Examples of useful contact herbicides include:

U. bipyridylium herbicides such as those in which the active entity is the 1,1'-dimethyl-4,4'-dipyridylium ion (common name paraquat) and those in which the active entity is the 1,1'-ethylene-2,2'-dipyridylium ion (common name diquat);

V. organoarsenical herbicides such as monosodium methanearsonate (common name MSMA); and W. amino acid herbicides such as N-(phosphonomethyl)-glycine (common name glyphosate) and its salts and esters.

The invention is now illustrated by, but in no way limited to, the following Examples.

EXAMPLE 1

2-[1-(Ethoxyimino)propyl]-3-hydroxy-5-(4-methylthiophenyl)cyclohex-2-en-1-one (1)

(i) An aqueous solution of 10% sodium hydroxide (2.6 ml) was added dropwise to a solution of 4-methylthiobenzaldehyde (15.0 g; 98.7 mmole) in acetone (30 ml) and water (10 ml) the temperature of the reaction mixture being maintained below 30° C. during the addition. On completion of the reaction (ca 3 hrs) the reaction mixture was poured into water and the aqueous mixture was extracted with dichloromethane. The organic phase was separated, washed with water, dried over anhydrous magnesium sulfate, and the solvent was evaporated to give 1-(4-methylthiophenyl)but-1-en-3-one (14.0 g) as a crystalline solid, mp 100° C.

(ii) Diethyl malonate (7.3 g; 45.4 mmole) was added to a solution of sodium metal (1.0 g; 42.9 mmole) in anhydrous absolute ethanol (100 ml). 1-(4-Methylthiophenyl)but-1-en-3-one (9.0 g; 43.7 mmole) was added to the solution and the mixture was heated under reflux, under nitrogen, with stirring for a period of 4 hours. An aqueous solution of potassium hydroxide (5.3 g in 30 ml of water) was added and the mixture was heated under reflux for a further 4 hours. The solution was poured into water, acidified with dilute aqueous hydrochloric acid and extracted with ethyl acetate. The organic phase was extracted with an aqueous 10% sodium hydroxide solution, the aqueous extract was acidified with dilute aqueous hydrochloric acid extracted with ethyl acetate. The organic phase was washed with with water, dried over anhydrous sodium sulfate and the solvent was evaporated to give 3-hydroxy-5-(4-methylthiophenyl)cyclohex-2-en-1-one (7.6 g) as a yellow crystalline solid, mp 199° C.

(iii) Propionic anhydride (30 ml) was added cautiously to freshly prepared sodium methoxide (0.3 g). On completion of the reaction 3-hydroxy-5-(4-methylthiophenyl)cyclohex-2-en-1-one (6.0 g) was added and the reaction mixture was heated for a period of 75 minutes. The excess propionic anhydride was removed by distillation under reduced pressure. Aqueous 3M potassium hydroxide (40 ml) was added to the tarry residue and the mixture was heated under reflux for a period of 3 hours. The reaction mixture was cooled, poured into water (100 ml) and acidified with dilute hydrochloric acid. The aqueous mixture was extracted with diethyl ether, the organic phase was washed with water, dried over anhydrous sodium sulfate, and the solvent was evaporated to give a dark coloured solid. The product was purified by column chromatography over silica gel (eluant dichloromethane) to give 3-hydroxy-5-(4-methylthiophenyl)-2-propionylcyclohex-2-en-1-one (3.2 g) as a yellow crystalline solid, mp 91° C.

(iv) A solution of sodium hydroxide (0.15 g) in water (5 ml) and then ethoxyamine hydrochloride (0.37 g) were added to a solution of 3-hydroxy-5-(4-methylthiophenyl)-2-propionylcyclohex-2-en-1-one (1.0 g) in ethanol (40 ml). The mixture was stirred at room temperature and the progress of the reaction was monitored by thin layer chromatography on silica gel (eluant dichloromethane). On completion of the reaction the solvent was removed by distillation under reduced pressure. The residue was treated with dichloromethane and the organic phase was washed with water and dried over anhydrous sodium sulfate. The solvent was evaporated to give 2-[1-(ethoxyimino)propyl]-3-hydroxy-5-(4-methylthiophenyl)-cyclohex-2-en-1-one (0.95 g) as a yellow oil.

The product was characterized by proton nuclear magnetic resonance spectrosopy. Pmr spectrum (CDCl$_3$; δ in ppm): 1.33 (6H, m); 2.47 (3H, s); 2.68–3.33 (7H, m); 4.16 (2H, q); 7.21 (4H, m); 15.03 (1H, s).

EXAMPLE 2

2-[1-(Ethoxyimino)propyl]-3-hydroxy-5-[4-(n-butylthio)phenyl]cyclohex-2-en-1-one (2)

(a) A mixture of 4-nitrobenzaldehyde (10.0 g), potassium carbonate (10.0 g), n-butylthiol (12.5 ml) and dimethylformamide (12.5 ml) was heated at 100° C. for a period of 16 hours, cooled and poured into water (250 ml). The aqueous mixture was extracted with diethyl ether (4×250 ml) and the combined organic phases were washed with aqueous 2% sodium hydroxide solution (5×100 ml) and finally with water. The organic phase was dried over anhydrous sodium sulfate and the solvent was removed by distillation to give 4-(n-butylthio)benzaldehyde (10.8 g) as a reddish coloured oil. The product was characterized by proton nuclear magnetic resonance spectroscopy. Pmr (CDCl$_3$; δ in ppm): 0.97 (3H, t); 1.60 (4H, m); 3.03 (2H, t); 7.32 (2H, d); 7.77 (2H, d); 9.89 (1H, s).

(b) (i) 1-[4-(n-butylthio)phenyl]but-1-en-3-one was prepared from 4-(n-butylthio)benzaldehyde following essentially the same procedure as that described in Example 1 part (i). The product was characterized by proton nuclear magnetic resonance spectroscopy. Pmr (CDCl$_3$; δ in ppm): 0.93 (3H, t); c.a. 1.6 (4H, m); 2.37 (3H, s); 2.97 (2H, t); 6.67 (1H, d); 7.22–7.58 (5H, m).

(ii) 3-Hydroxy-5-[4-(n-butylthio)phenyl]cyclohex-2-en-1-one was prepared from 1-[4-(n-butylthio)-phenyl]but-1-en-3-one following essentially the same procedure as that described in Example 1 part (ii). The product was characterized by proton nuclear magnetic resonance spectroscopy. Pmr (D$_6$-DMSO; δ in ppm): 0.86 (3H,t); c.a. 1.46 (4H, m); 2.24–3.44 (7H, m); 5.28 (1H, s); 7.29 (4H, s).

(iii) A mixture of propionic anhydride (8.0 ml) and propionic acid (8.0 ml) was added to 3-hydroxy-5-[4-(n-butylthio)phenyl]cyclohex-2-en-1-one (4.0 g) and the mixture was heated at a temperature of 115° C. with stirring until a clear solution was obtained. Trifluoromethanesulfonic acid (10 drops) was then added and the heating and stirring was continued for a further 2 hours. The mixture was cooled and poured into water and the aqueous mixture was extracted with dichloromethane. The organic phase was washed with an aqueous solution of sodium hydrogen carbonate and then water, and was dried over anhydrous sodium sulfate. The solvent was evaporated to give an oil which was purified by column chromatography over silica gel (eluant dichloromethane) to give 3-hydroxy-5-[4-(n-butylthio)phenyl]-2-propionylcyclohex-2-en-1-one (3.8 g) as a cream coloured crystalline solid, mp 79° C.

(iv) 2-[1-(Ethoxyimino)propyl]-3-hydroxy-5-[4-(n-butylthio)phenyl]cyclohex-2-en-1-one was prepared from 3-hydroxy-5-[4-(n-butylthio)phenyl]-2-propionylcyclohex-2-en-1-one following essentially the same procedure as that described in Example 1 part (iv). The product was obtained as an oil and was characterized by proton nuclear magnetic resonance spectroscopy. Pmr spectrum (CDCl$_3$; δ in ppm): 0.91–1.39 (13H, m); 2.74–3.00 (9H, m); 3.98–4.22 (2H, q); 7.25 (4H, m); 14.97 (1H, s).

EXAMPLE 3

The following compounds were prepared following essentially the same procedure as that described in Example 2. (The intermediate 3-hydroxy-5-[4-(n-butylthio)phenyl]-2-butyrylcyclohex-2-en-1-one was characterized by proton magnetic resonance spectroscopy. Pmr spectrum (CDCl$_3$; δ in ppm): 0.83–1.06 (6H, 2xt); c.a. 1.6 (6H, m); c.a. 2.6–3.4 (9H, m); 7.23 (4H, q); 18.31 (1H, s).) The compounds were obtained as oils and were characterized by proton nuclear magnetic resonance spectroscopy.

(a) 2-[1-(ethoxyimino)butyl]-3-hydroxy-5-[4-(n-butylthio)phenyl]cyclohex-2-en-1-one (9), pmr (CDCl$_3$; δ in ppm): 0.89–1.55 (15H, m); 2.83–3.03 (9H, m); 3.99–4.23 (2H, q); 7.2 (4H, m); 15.04 (1H, s); and (b) 2-[1-(allyloxyimino)butyl]-3-hydroxy-5-[4-(n-butylthio)phenyl]cyclohex-2-en-1-one (10), pmr (CDCl$_3$; δ in ppm): 0.84–1.72 (12H, m); 2.67–3.03 (9H, m); 4.50 (2H, d); 5.25–5.46 (2H, m); 5.70–6.10 (1H, m); 7.30 (4H, m); 14.72 (1H, s).

EXAMPLE 4

Sodium salt of 2-[1-(ethoxyimino)propyl]-3-hydroxy-5-(4-methylthiophenyl)cyclohex-2-en-1-one (3)

A solution of sodium hydroxide (0.036 g) in water (1 ml) was added to a solution of 2-[1-(ethoxyimino)propyl]-3-hydroxy-5-(4-methylthiophenyl)cyclohex-2-en-1-one (0.30 g) in toluene (25 ml). The solvent was removed by distillation under vacuum to yield the title compound as a yellow solid (0.31 g), mp decomposes above 150° C.

EXAMPLE 5

2-[1-(Ethoxyimino)propyl]-3-hydroxy-5-[3-nitro-4-(n-butylthio)phenyl]cyclohex-2-en-1-one (11)

(a) 4-Chloro-3-nitrobenzaldehyde (25.0 g) was added to a solution of sodium n-butylthiolate (1 equiv; prepared by addition of n-butylthiol to an equimolar amount of sodium dissolved in absolute alcohol) in absolute alcohol (300 ml) and the mixture was heated under reflux for 4 hr. On cooling, the mixture was filtered and the filtrate was evaporated under reduced pressure. The residue was purified by column chromatography over silica gel with dichloromethane elution to give 3-nitro-4-(n-butylthio)benzaldehyde as yellow crystals, mp 93° C. Pmr spectrum (CDCl$_3$; δ in ppm): 0.99 (3H, t); 1.66 (4H, m); 3.04 (2H, t); 7.56 (1H, d); 8.05 (1H, dofd); 8.69 (1H, d); 10.00 (1H, s).

(b) (i) A mixture of 3-nitro-4-(n-butylthio)-benzaldehyde (12.0 g), 1-triphenylphosphoranylidene-2-propanone (1.2 equiv.) dimethyl sulfoxide (300 ml) was stirred at ambient temperature for 24 hr. The solution was poured into water (1 liter) and the resulting mixture was extracted with ethyl acetate. The dried (MgSO$_4$) organic extract was evaporated under reduced pressure and the residue was purified by column chromatography over silica with chloroform elution to give cis-1-[3-nitro-4-(n-butylthio)phenyl]-but-1-en-3-one, mp 100° C. Pmr spectrum (CDCl$_3$; δ in ppm): 0.97 (3H, t); 1.63 (4H, m); 2.40 (3H, s); 2.98 (2H, t); 6.75 (1H, d); 7.38–7.75 (3H, m); 8.36 (1H, d).

(ii) 3-Hydroxy-5-[3-nitro-4-(n-butylthio)phenyl]cyclohex-2-en-1-one was prepared from cis-1-[3-nitro-4-(n-butylthio)phenyl]but-1-en-3-one following essentially the same procedure as that described in Example 1 part (ii).

(iii) 3-Hydroxy-5-[3-nitro-4-(n-butylthio)phenyl]-2-propionylcyclohex-2-en-1-one was prepared from 3-hydroxy-5-[3-nitro-4-(n-butylthio)phenyl]cyclohex-2-en-1-one following essentially the same procedure as that described in Example 1 part (iii). The product was obtained as yellow crystals, mp 102° C. Pmr spectrum (CDCl$_3$; δ in ppm): 0.98 (3H, t); 1.18 (3H, t); 1.67 (4H, m); 2.70–3.56 (9H, m); 7.46 (2H, s); 8.10 (1H, s); 18.34 (1H, s).

(iv) 2-[1-(Ethoxyimino)propyl]-3-hydroxy-5-[3-nitro-4-(n-butylthio)phenyl]cyclohex-2-en-1-one was prepared from 3-hydroxy-5-[3-nitro-4-(n-butylthio)phenyl]-2-propionylcyclohex-2-en-1-one following essentially the same procedure as that described in Example 1 part (iv). Pmr spectrum (CDCl$_3$; δ in ppm): 0.86–1.84 (13H, m); 2.66–3.62 (9H, m); 4.13 (2H, q); 7.43 (2H, s); 8.07 (1H, s); 15.12 (1H, brs).

EXAMPLE 6

2-[1-(Ethoxyimino)propyl]-3-hydroxy-5-[3-(N,N-dimethyl-sulfonamido)-4-(methylthio)phenyl]cyclohex-2-en-1-one (12)

(a) (i) Chlorosulfonic acid (9.5 ml) was added dropwise to a solution of 3-hydroxy-5-[4-(methylthio)-phenyl]-2-propionylcyclohex-2-en-1-one (2.4 g) in chloroform (18 ml) at 0° C. After 15 hr, the solution was warmed to ambient temperature and after a further 3 hr the mixture was poured onto ice. The resulting mixture was extracted with dichloromethane and the organic extract was washed with water. Evaporation of the solvent gave 3-hydroxy-5-[3-chlorosulfonyl-4-(methylthio)phenyl]-2-propionylcyclohex-2-en-1-one (2.42 g). Pmr spectrum (CDCl$_3$; δ in ppm): 1.14 (3H, t); 2.61 (3H, t); c.a. 2.6–3.68 (7H, m); 7.39–7.70 (2H, m); 7.94 (1H, s); 18.20 (1H, s).

(ii) 3-Hydroxy-5-[3-chlorosulfonyl-4-(methylthio)phenyl]-2-propionylcyclohex-2-en-1-one (1.2 g) was added in portions to a stirred solution of dimethylamine (33% in ethanol) and aqueous ethanol (1:1 v/v; 60 ml) at 0° C. After 0.5 hr at ambient temperature, hydrochloric acid was added to give a solution of pH3. The solvent was partially evaporated at reduced pressure and the residue was poured into water. The mixture was extracted with dichloromethane and evaporation of the organic solvent gave 3-hydroxy-5-[3-(N,N-dimethylsulfonamido)-4-(methylthio)phenyl]cyclohex-2-en-1-one, mp 197° C. Pmr spectrum (CDCl$_3$; δ in ppm): 1.15 (3H, t); 2.52 (3H, t); 2.84 (6H, s); 2.67–3.56 (7H, m); 7.36 (2H, s); 7.85 (1H, s); 18.25 (1H, s).

(b) 2-[1-(Ethoxyimino)propyl]-3-hydroxy-5-[3-(N,N-dimethylsulfonamido)-4-(methylthio)phenyl]cyclohex-2-en-1-one was prepared from 3-hydroxy-5-[3-(N,N-dimethylsulfonamido)-4-(methylthio)phenyl]cyclohex-2-en-1-one following essentially the same procedure as that described in Example 1 part (iv), except dimethylformamide instead of ethanol was used as solvent. Pmr spectrum (CDCl$_3$; δ in ppm): 1.09–1.42 (6H, 2xt); 2.50 (3H, s); 2.84 (6H, s); 2.67–3.62 (7H, m); 4.13 (2H, q); 7.33 (2H, m); 7.82 (1H, m).

EXAMPLE 7

2-[1-(Ethoxyimino)propyl]-3-hydroxy-5-[3-(methylthio)phenyl]cyclohex-2-en-1-one (13)

(i) 1-[3-Methylthio)phenyl]but-1-en-3-one was prepared from 3-(methylthio)benzaldehyde following essentially the same procedure as that described in Example 1 part (i). Pmr spectrum (CDCl$_3$; δ in ppm): 2.37 (3H, s); 2.50 (3H,s); 6.70 (1H, d); 7.30–7.56 (5H, m).

(ii) 3-Hydroxy-5-[3-(methylthio)phenyl]cyclohex-2-en-1-one was prepared from 1-[3-(methylthio)phenyl]but-1-en-3-one following essentially the same procedure as that described in Example 1 part (ii); mp 141° C.

(iii) Sodium hydride (0.077 g) was added to 3-hydroxy-5-[3-(methylthio)phenyl]cyclohex-2-en-1-one (0.58 g) in dry dimethylformamide (5 ml) at 80° C.

After 10 mins, propionic anhydride (0.42 g) was added and the mixture was heated at 100° C. for 2 hr. The cooled solution was poured into water and the resulting mixture was extracted with ethyl acetate. After evaporation of the organic extract the residue was purified by column chromatography over silica with ethyl acetate/dichloromethane (1:1 v/v) elution to give 3-hydroxy-5-[3-(methylthio)phenyl]-2-propionylcyclohex-2-en-1-one. Pmr spectrum (CDCl$_3$; δ in ppm): 1.16 (3H, t); 2.49 (3H, s); 2.30–3.39 (7H, m); 6.95–7.26 (4H, m); c.a. 18.3 (1H, brs).

(iv) 2-[1-(Ethoxyimino)propyl]-3-hydroxy-5-[3-(methylthio)phenyl]cyclohex-2-en-1-one was prepared from 3-hydroxy-5-[3-(methylthio)phenyl]-2-propionylcyclohex-2-en-1-one following essentially the same procedure as that described in Example 1 part (iv). Pmr spectrum (CDCl$_3$; δ in ppm): 1.08–1.41 (6H, 2xt); 2.48 (3H, s); c.a. 2.4–3.50 (7H, m); 4.12 (2H, q); 7.0–7.3 (4H, m); 15.1 (1H, brs).

EXAMPLE 8

This non-limiting Example illustrates the preparation of formulations of the compounds of the invention.

(a) Emulsifiable Concentrate

Compound No. 1 was dissolved in toluene containing 7% v/v "Teric" N13 and 3% v/v "Kemmat" SC15B to give an emulsifiable concentrate which may be diluted with water to the required concentration to give an aqueous emulsion which may be applied by spraying.

("Teric" is a Trade Mark and "Teric" N13, is a product of ethoxylation of nonylphenol; "Kemmat" is a Trade Mark and "Kemmat" SC15B is a formulation of calcium dodecylbenzenesulfonate.)

(b) Aqueous Suspension

Compound No. 1 (5 parts by weight) and "Dyapol" PT (1 part by weight) was added to an aqueous solution (94 parts by weight) of "Teric" N8 and the mixture was ball milled to produce a stable aqueous suspension which may be diluted with water to the required concentration to give an aqueous suspension which may be applied by spraying. ("Dyapol" is a Trade Mark and "Dyapol" PT is an anionic suspending agent; "Teric" N8 is a product of ethoxylation of nonylphenol.)

(c) Emulsifiable Concentrate

Compound No. 1 (10 parts by weight), "Teric" N13 (5 parts by weight) and "Kemmat" SC15B (5 parts by weight) were dissolved in "Solvesso" 150 (80 parts by weight) to give an emulsifiable concentrate which may be diluted with water to the required concentration to give an aqueous emulsion which may be applied by spraying. ("Solvesso" is a Trade Mark and "Solvesso" 150 is a high boiling point aromatic petroleum fraction.)

(d) Dispersible Powder

Compound No. 1 (10 parts by weight), "Matexil" DA/AC (3 parts by weight), "Aerosol" OT/B (1 part by weight) and china clay 298 (86 parts by weight) were blended and then milled to give a powder composition having a particle size below 50 microns. ("Matexil" is a Trade Mark and "Matexil" DA/AC is the disodium salt of a naphthalenesulfonic acid/formaldehyde condensate; "Aerosol" is a Trade Mark and "Aerosol" OT/B is a formulation of the dioctyl ester of sodium sulfosuccinic acid.)

(e) High Strength Concentrate

Compound No. 1 (99 parts by weight), silica aerogel (0.5 parts by weight) and synthetic amorphous silica (0.5 parts by weight) were blended and ground in a hammer-mill to produce a powder having a particle size less than 200 microns.

(f) Dusting Powder

Compound No. 1 (10 parts by weight), attapulgite (10 parts by weight) and pyrophyllite (80 parts by weight) were thoroughly blended and then ground in a hammer-mill to produce a powder of particle size less than 200 microns.

Emulsifiable concentrates and/or suspensions of the compounds of the invention were prepared essentially as described in part (a), (b) or (c) above and then diluted with water, optionally containing a surface active agent and/or oil, to give aqueous compositions of the required concentration which were used, as described in Examples 9 and 10, in the evaluation of the pre-emergence and post-emergence herbicidal activity of the compounds.

EXAMPLE 9

The pre-emergent herbicidal activity of the compounds of the invention formulated as described in Example 8 was assessed by the following procedure:

The seeds of the test species were sown in rows 2 cm deep in soil contained in seed boxes. The monocotyledonous plants and the dicotyledonous plants were sown in separate boxes and after sowing the two boxes were sprayed with the required quantity of a composition of the invention. Two duplicate seed boxes were prepared in the same manner but were not sprayed with a composition of the invention and were used for comparison purposes. All the boxes were placed in a glasshouse, lightly watered with an overhead spray to initiate germination and then sub-irrigated as required for optimum plant growth. After three weeks the boxes were removed from the glass house and the effects of the treatment was visually assessed. The results are presented in Table 2 where the damage to plants is rated on a scale of from 0 to 5 where 0 represents from 0 to 10% damage, 1 represents from 11 to 30% damage, 2 represents from 31 to 60% damage, 3 represents from 61 to 80% damage, 4 represents from 81 to 99% damage and 5 represents 100% kill. A dash (-) means that no experiment was carried out.

The names of the test plants are as follows:

| | |
|---|---|
| Wh | Wheat |
| Ot | Wild Oats |
| Rg | Ryegrass |
| Jm | Japanese millet |
| P | Peas |
| Ip | Ipomea |
| Ms | Mustard |
| Sf | Sunflower |

TABLE 2

PRE-EMERGENCE HERBICIDAL ACTIVITY

| Compound No | APPLICATION Rate (kg/ha) | Wh | Ot | Rg | Jm | P | Ip | Ms | Sf |
|---|---|---|---|---|---|---|---|---|---|
| 1 | 2.0 | 4 | 5 | 5 | 5 | 0 | 0 | 0 | 0 |
| 1 | 0.5 | 1 | 1 | 5 | 4 | 0 | 0 | 0 | 0 |
| 1 | 0.25 | 0 | 1 | 3 | 1 | 0 | 0 | 0 | 0 |
| 1 | 0.125 | 0 | 2 | 2 | 1 | 0 | 0 | 0 | 0 |
| 2 | 1.0 | 1 | 2 | 2 | 0 | 0 | 0 | 0 | 0 |
| 3 | 2.0 | 3 | 5 | 5 | 5 | 0 | 0 | 0 | 0 |
| 3 | 0.5 | 0 | 1 | 5 | 4 | 0 | 0 | 0 | 0 |
| 9 | 1.0 | 0 | 0 | 4 | 4 | 0 | 0 | 0 | 0 |
| 11 | 0.5 | 0 | 0 | 0 | 1 | 0 | 0 | 0 | 0 |
| 12 | 0.5 | 0 | 0 | 3 | 4 | 0 | 0 | 0 | 0 |

EXAMPLE 10

The post-emergent herbicidal activity of the compounds of the invention formulated as described in Example 8 was assessed by the following procedure.

The seeds of the test species were sown in rows 2 cm deep in soil contained in seed boxes. The monocotyledonous plants and the dicotyledonous plants were sown in separate seed boxes in duplicate. The four seed boxes were placed in a glasshouse, lightly watered with an overhead spray to initiate germination and then sub-irrigated as required for optimum plant growth. After the plants had grown to a height of about 10 to 12.5 cm one box of each of the monocotyledonous plants and the dicotyledonous plants was removed from the glasshouse and sprayed with the required quantity of a composition of the invention. After spraying the boxes were returned to the glass house for a further 3 weeks and the effect of treatment was visually assessed by comparison with the untreated controls. The results are presented in Table 3 where the damage to plants is rated on a scale of from 0 to 5 where 0 represents from 0 to 10% damage, 1 represents from 11 to 30% damage, 2 represents from 31 to 60% damage, 3 represents from 61 to 80% damage, 4 represents from 81 to 99% damage and 5 represents 100% kill. A dash (-) means that no experiment was carried out.

The names of the test plants are as follows:

| | |
|---|---|
| Wh | Wheat |
| Ot | Wild Oats |
| Rg | Ryegrass |
| Jm | Japanese millet |
| P | Peas |
| Ip | Ipomea |
| Ms | Mustard |
| Sf | Sunflower |

TABLE 3

POST-EMERGENCE HERBICIDAL ACTIVITY

| Compound No | APPLICATION Rate (kg/ha) | Wh | Ot | Rg | Jm | P | Ip | Ms | Sf |
|---|---|---|---|---|---|---|---|---|---|
| 1 | 2.0 | 5 | 5 | 5 | 5 | 0 | 0 | 0 | 0 |
| 1 | 0.5 | 5 | 5 | 5 | 5 | 0 | 0 | 0 | 0 |
| 1 | 0.25 | 5 | 5 | 5 | 5 | 0 | 0 | 0 | 0 |
| 1 | 0.125 | 4 | 5 | 5 | 5 | 0 | 0 | 0 | 0 |
| 1 | 0.0625 | 2 | 4 | 5 | 4 | 0 | 0 | 0 | 0 |
| 2 | 1.0 | 4 | 5 | 5 | 5 | 0 | 0 | 0 | 0 |
| 2 | 0.5 | 4 | 5 | 5 | 5 | 0 | 0 | 0 | 0 |
| 2 | 0.25 | 4 | 5 | 5 | 5 | 0 | 0 | 0 | 0 |
| 2 | 0.125 | 1 | 4 | 4 | 4 | 0 | 0 | 0 | 0 |
| 3 | 2.0 | 5 | 5 | 5 | 5 | 0 | 0 | 0 | 0 |
| 3 | 0.5 | 3 | 5 | 5 | 5 | 0 | 0 | 0 | 0 |
| 9 | 1.0 | 4 | 5 | 5 | 5 | 0 | 0 | 0 | 0 |
| 9 | 0.5 | 3 | 5 | 5 | 5 | 0 | 0 | 0 | 0 |
| 9 | 0.25 | 0 | 5 | 3 | 5 | 0 | 0 | 0 | 0 |
| 10 | 1.0 | 3 | 5 | 5 | 5 | 0 | 0 | 0 | 0 |
| 10 | 0.5 | 2 | 5 | 5 | 5 | 0 | 0 | 0 | 0 |
| 10 | 0.25 | 1 | 5 | 5 | 5 | 0 | 0 | 0 | 0 |
| 11 | 0.5 | 1 | 5 | 5 | 5 | 0 | 0 | 0 | 0 |
| 12 | 0.5 | 3 | 3 | 5 | 5 | 0 | 0 | 0 | 0 |
| 12 | 0.25 | 3 | 3 | 4 | 5 | 0 | 0 | 0 | 0 |

EXAMPLE 11

The compounds were formulated for test by mixing an appropriate amount with 5 ml of an emulsion prepared by diluting 160 ml of a solution containing 21.9 g per liter of "Span" 80 and 78.2 g per liter of "Tween" 20 in methylcyclohexanone to 500 ml with water. "Span" 80 is a Trade Mark for a surface-active agent comprising sorbitan monolaurate. "Tween" 20 is a Trade Mark for a surface-active agent comprising a condensate of sorbitan monolaurate with 20 molar proportions of ethylene oxide. Each 5 ml emulsion containing a test compound was then diluted to 40 ml with water and sprayed on to young pot plants (post-emergence test) of the species named in Table 4 below. Damage to test plants was assessed after 14 days on a scale of 0 to 5 where 0 is 0 to 20% damage and 5 is complete kill. In a test for pre-emergence herbicidal activity, seeds of the test plants were sown in a shallow slit formed in the surface of soil in fibre trays. The surface was then levelled and sprayed, and fresh soil then spread thinly over the sprayed surface. Assessment of herbicidal damage was carried out after 21 days using the same scale of 0 to 5 as the post-emergence test. In both cases the degree of herbicidal damage was assessed by comparison with untreated control plants. The results are given in Table 4 below. A dash (-) means that no experiment was carried out.

The names of the test plants were as follows:

| | |
|---|---|
| Sb | Sugar beet |
| Rp | Rape |
| Ct | Cotton |
| Sy | Soy bean |
| Mz | Maize |
| Ww | Winter wheat |
| Rc | Rice |
| Sn | *Senecio vulgaris* |
| Ip | *Ipomea purpurea* |
| Am | *Amaranthus retroflexus* |
| Pi | *Polygonum aviculare* |
| Ca | *Chenopodium album* |
| Ga | *Galium aparine* |
| Xa | *Xanthium pensylvanicum* |
| Ab | *Abutilon theophrasti* |
| Co | *Cassia obtusifolia* |
| Av | *Avena fatua* |
| Dg | *Digitaria sanguinalis* |
| Al | *Alopecurus myosuroides* |
| St | *Setaria viridis* |
| Ec | *Echinochloa crus-galli* |
| Sh | *Sorghum halepense* |
| Ag | *Agropyron repens* |
| Cn | *Cyperus rotundas* |

$R^1$ is selected from $C_1$ to $C_6$ alkyl;
A is selected from hydrogen and nitro;
$R^2$ is selected from the group consisting of hydrogen and the cations of the alkali metal ions;
$R^3$ is selected from ethyl and allyl; and
$R^4$ is selected from ethyl and n-propyl.

2. A compound according to claim 1 of formula

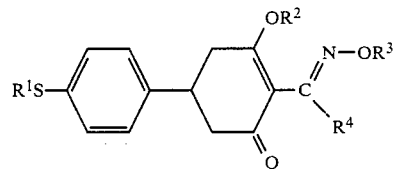

wherein:
$R^1$ is selected from methyl and n-butyl;
$R^2$ is selected from hydrogen and sodium;
$R^3$ is selected from ethyl and allyl; and
$R^4$ is selected from ethyl and n-propyl.

3. The compound 2-[1-(ethoxyimino)propyl]-3-hydroxy-5-[4-(methylthio)phenyl]cyclohex-2-en-1-one.

4. The compound 5-[4-(n-butylthio)phenyl]-2-[1-(ethoxyimino)propyl]-3-hydroxycyclohex-2-en-1-one.

5. A herbicidal composition comprising an active ingredient, an effective amount of a compound as defined according to claim 1 and a carrier therefor.

6. A process for severely damaging or killing unwanted plants which process comprises applying to said plants, or to the growth medium of said plants, an effective amount of a compound as defined according to claim 1.

TABLE 4

| Com- No | APPLICATION Method (kg/ha) | Sb | Rp | Ct | Sy | Mz | Ww | Rc | Sn | Ip | Am | Pi | Ca | Ga | Xa | Ab | Co | Av | Dg | Al | St | Ec | Sh | Ag | Cn |
|---|---|---|---|---|---|---|---|---|---|---|---|---|---|---|---|---|---|---|---|---|---|---|---|---|---|
| 1 | PRE 0.2 | 0 | 2 | 1 | 1 | 0 | 2 | 3 | 1 | 0 | 0 | — | 0 | 0 | 0 | 2 | 1 | 5 | 5 | 5 | 5 | 5 | 5 | 5 | 0 |
| 1 | PRE 0.05 | 1 | 0 | 0 | 1 | 3 | 4 | 5 | 2 | 1 | 0 | — | 0 | 1 | 0 | 0 | 0 | 4 | 2 | 4 | 5 | 5 | 2 | 4 | 0 |
| 1 | POST 0.2 | 0 | 0 | 0 | 0 | 4 | 4 | 4 | 0 | 2 | 1 | — | 0 | 0 | 0 | 0 | 1 | 5 | 5 | 4 | 5 | 5 | 5 | 4 | 0 |
| 1 | POST 0.05 | 1 | 0 | 0 | 0 | 4 | 2 | 3 | 0 | 0 | 0 | — | 0 | 0 | 0 | 0 | 2 | 4 | 4 | 4 | 4 | 5 | 5 | 2 | 0 |
| 9 | PRE 0.4 | — | — | — | — | 1 | 0 | 2 | — | — | — | — | — | — | — | — | — | 3 | 1 | 5 | 4 | 5 | 2 | 5 | — |
| 9 | POST 0.4 | — | — | — | — | 4 | 3 | 4 | — | — | — | — | — | — | — | — | — | 4 | 4 | 3 | 3 | 4 | 4 | 2 | — |
| 10 | PRE 0.4 | — | — | — | — | 0 | 0 | 2 | — | — | — | — | — | — | — | — | — | 2 | 1 | 5 | 4 | 5 | 1 | 0 | — |
| 10 | POST 0.4 | — | — | — | — | 4 | 2 | 3 | — | — | — | — | — | — | — | — | — | 4 | 4 | 2 | 3 | 5 | 4 | 1 | — |
| 12 | PRE 1.0 | — | — | — | — | 5 | 5 | 5 | — | — | — | — | — | — | — | — | — | 5 | 5 | 5 | 5 | 5 | 5 | — | — |
| 12 | PRE 0.2 | — | — | — | — | 3 | 3 | 4 | — | — | — | — | — | — | — | — | — | 4 | 4 | 5 | 5 | 5 | 4 | — | — |
| 12 | POST 1.0 | — | — | — | — | 4 | 4 | 4 | — | — | — | — | — | — | — | — | — | 5 | 5 | 4 | 4 | 5 | 5 | 4 | — |
| 12 | POST 0.2 | — | — | — | — | 4 | 3 | 3 | — | — | — | — | — | — | — | — | — | 4 | 4 | 4 | 4 | 4 | 4 | 4 | — |

We claim:
1. A compound of formula

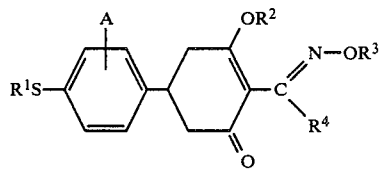

wherein:

tive amount of a compound as defined according to claim 1.

7. A process for selectively controlling the growth of monocotyledonous weeds in dicotyledonous crops which process comprises applying to said crop, or to the growth medium of said crop, a compound as defined according to claim 1 in an amount sufficient to severely damage or or kill said weeds but insufficient to substantially damage said crop.

8. A process according to claim 6 or claim 7 wherein the compound is applied at a rate in the range of from 0.005 to 20 kilograms per hectare.

* * * * *